US010169862B2

(12) United States Patent
André et al.

(10) Patent No.: US 10,169,862 B2
(45) Date of Patent: Jan. 1, 2019

(54) METHODS AND SYSTEMS FOR LASER SPECKLE IMAGING OF TISSUE USING A COLOR IMAGE SENSOR

(71) Applicant: Novadaq Technologies ULC, Burnaby (CA)

(72) Inventors: Marc André, Spiegel (CH); Arthur E. Bailey, North Vancouver (CA); Paul Roald Westwick, Vancouver (CA)

(73) Assignee: NOVADAQ TECHNOLOGIES ULC (CA)

(*) Notice: Subject to any disclaimer, the term of this patent is extended or adjusted under 35 U.S.C. 154(b) by 128 days.

(21) Appl. No.: 15/148,959

(22) Filed: May 6, 2016

(65) Prior Publication Data
US 2016/0328848 A1 Nov. 10, 2016

Related U.S. Application Data

(60) Provisional application No. 62/158,298, filed on May 7, 2015.

(51) Int. Cl.
*G06T 7/00* (2017.01)
*H04N 1/48* (2006.01)
(Continued)

(52) U.S. Cl.
CPC .......... *G06T 7/0012* (2013.01); *A61B 5/0059* (2013.01); *A61B 5/0261* (2013.01);
(Continued)

(58) Field of Classification Search
CPC ............... G06T 7/0012; G06T 7/90; G06T 2207/10024; G06T 2207/30104;
(Continued)

(56) References Cited

U.S. PATENT DOCUMENTS

| 4,862,894 A | 9/1989 | Fujii |
| 5,267,016 A | 11/1993 | Meinzer et al. |

(Continued)

FOREIGN PATENT DOCUMENTS

| CN | 101926644 A | 12/2010 |
| DE | 10 2008 017 390 A1 | 10/2009 |

(Continued)

OTHER PUBLICATIONS

Golpayegani et al. "Laser Doppler and Laser Speckle Techniques for Blood flow Measurement." 2nd International Conference on Bioinformatics and Biomedical Engineering, May 16, 2008, pp. 1555-1560.*

(Continued)

*Primary Examiner* — Jon Chang
(74) *Attorney, Agent, or Firm* — Morrison & Foerster LLP

(57) ABSTRACT

Methods and systems for imaging tissue of a subject are disclosed, and involve illuminating the tissue with a coherent light having a coherent wavelength, acquiring image data of the tissue using a color image sensor, and processing the image data using laser speckle contrast analysis while correcting for differences in sensitivity of color pixels at the coherent wavelength to generate a perfusion image of the tissue. The perfusion image is then displayed to the user. Also disclosed are methods and systems for correcting ambient light and for acquiring white light images along with laser speckle images.

19 Claims, 12 Drawing Sheets
(7 of 12 Drawing Sheet(s) Filed in Color)

(51) Int. Cl.
*H04N 1/60* (2006.01)
*G06T 7/90* (2017.01)
*A61B 5/026* (2006.01)
*A61B 5/00* (2006.01)
*G01N 21/47* (2006.01)

(52) U.S. Cl.
CPC .............. *G06T 7/90* (2017.01); *H04N 1/482* (2013.01); *H04N 1/603* (2013.01); *H04N 1/6086* (2013.01); *A61B 5/0062* (2013.01); *A61B 5/445* (2013.01); *G01N 2021/479* (2013.01); *G06T 2207/10004* (2013.01); *G06T 2207/10024* (2013.01); *G06T 2207/30104* (2013.01)

(58) Field of Classification Search
CPC .......... G06T 2207/10004; H04N 1/482; H04N 1/603; H04N 1/6086; A61B 5/0059; A61B 5/0261; A61B 5/445; A61B 5/0062; G01N 2021/479
See application file for complete search history.

(56) References Cited

U.S. PATENT DOCUMENTS

| | | |
|---|---|---|
| 5,685,313 A | 11/1997 | Mayevsky |
| 6,045,511 A | 4/2000 | Ott et al. |
| 6,178,340 B1 | 1/2001 | Svetliza |
| 6,263,227 B1 | 7/2001 | Boggett et al. |
| 6,485,413 B1 | 11/2002 | Boppart et al. |
| 6,728,561 B2 | 4/2004 | Smith et al. |
| 6,970,729 B2 | 11/2005 | Hartmann |
| 7,113,817 B1 | 9/2006 | Winchester, Jr. et al. |
| 7,123,363 B2 | 10/2006 | Puttappa et al. |
| 7,231,243 B2 | 6/2007 | Tearney et al. |
| 7,483,062 B2 | 1/2009 | Allman et al. |
| 7,519,212 B2 | 4/2009 | Brady et al. |
| 8,185,176 B2 | 5/2012 | Mangat et al. |
| 8,298,521 B2 | 10/2012 | Schwartz et al. |
| 8,480,579 B2 | 7/2013 | Serov et al. |
| 9,066,686 B2 | 6/2015 | Lasser et al. |
| 9,757,039 B2 | 9/2017 | Lasser et al. |
| 2002/0052551 A1 | 5/2002 | Sinclair et al. |
| 2002/0082480 A1 | 6/2002 | Riff et al. |
| 2003/0023153 A1 | 1/2003 | Izatt et al. |
| 2003/0118649 A1 | 6/2003 | Gao et al. |
| 2003/0137669 A1 | 7/2003 | Rollins et al. |
| 2004/0034294 A1 | 2/2004 | Kimball et al. |
| 2004/0176701 A1 | 9/2004 | Fujii |
| 2004/0225222 A1 | 11/2004 | Zeng et al. |
| 2005/0187477 A1 | 8/2005 | Serov et al. |
| 2005/0206583 A1 | 9/2005 | Lamelson et al. |
| 2006/0064024 A1 | 3/2006 | Schnall |
| 2006/0111620 A1 | 5/2006 | Squilla et al. |
| 2007/0016079 A1 | 1/2007 | Freeman et al. |
| 2007/0100245 A1 | 5/2007 | Kashima |
| 2007/0139613 A1 | 6/2007 | Tanifuji et al. |
| 2007/0188707 A1 | 8/2007 | Nanjo |
| 2007/0225606 A1 | 9/2007 | Naghavi et al. |
| 2007/0239034 A1 | 10/2007 | Knoche et al. |
| 2007/0291277 A1 | 12/2007 | Everett et al. |
| 2008/0017787 A1 | 1/2008 | Okawa et al. |
| 2008/0021329 A1 | 1/2008 | Wood et al. |
| 2008/0100612 A1 | 5/2008 | Dastmalchi et al. |
| 2008/0241199 A1 | 10/2008 | Silverman |
| 2008/0294047 A1 | 11/2008 | Kodama et al. |
| 2009/0054788 A1 | 2/2009 | Hauger et al. |
| 2009/0130650 A1 | 5/2009 | Tan et al. |
| 2009/0192358 A1 | 7/2009 | Jaffer et al. |
| 2010/0049055 A1 | 2/2010 | Freudenberg et al. |
| 2010/0099992 A1 | 4/2010 | Holschneider et al. |
| 2010/0113940 A1 | 5/2010 | Sen et al. |
| 2010/0191541 A1 | 7/2010 | Prokoski |
| 2011/0013002 A1 | 1/2011 | Thompson et al. |
| 2011/0090325 A1 | 4/2011 | Hauger et al. |
| 2011/0099031 A1 | 4/2011 | Nair |
| 2012/0071765 A1 | 3/2012 | Chinnock |
| 2012/0078113 A1 | 3/2012 | Whitestone et al. |
| 2012/0277559 A1* | 11/2012 | Kohl-Bareis ........ A61B 5/0261 600/324 |
| 2013/0172735 A1 | 7/2013 | Andre et al. |
| 2013/0223705 A1 | 8/2013 | Ferguson, Jr. et al. |
| 2013/0296715 A1 | 11/2013 | Lasser et al. |
| 2014/0049779 A1* | 2/2014 | Tin ........................ G01B 11/30 356/456 |
| 2015/0080742 A1 | 3/2015 | Andre et al. |
| 2015/0198797 A1 | 7/2015 | Andre et al. |

FOREIGN PATENT DOCUMENTS

| | | |
|---|---|---|
| EP | 0763998 A1 | 3/1997 |
| EP | 1210910 A1 | 6/2002 |
| EP | 1241979 A1 | 9/2002 |
| EP | 1982645 A1 | 10/2008 |
| JP | S63-214238 A | 9/1988 |
| JP | H10-508763 A | 9/1998 |
| JP | H11-142748 A | 5/1999 |
| JP | 2003-516795 A | 5/2003 |
| JP | 2003-527700 A | 9/2003 |
| JP | 2004-267308 A | 9/2004 |
| JP | 2005-515818 A | 6/2005 |
| JP | 2005-532393 A | 10/2005 |
| JP | 2006-180926 A | 7/2006 |
| JP | 2007-315827 A | 12/2007 |
| JP | 2008-142355 A | 6/2008 |
| JP | 2008-541891 A | 11/2008 |
| JP | 2008-289870 A | 12/2008 |
| JP | 2010-532699 A | 10/2010 |
| JP | 2011-027895 A | 2/2011 |
| JP | 2012-113191 A | 6/2012 |
| WO | WO-1995/32664 A1 | 12/1995 |
| WO | WO-2001/43628 A1 | 6/2001 |
| WO | WO-03/063677 A1 | 8/2003 |
| WO | WO-2005/099572 A1 | 10/2005 |
| WO | WO-2005/099582 A1 | 10/2005 |
| WO | WO-2006/111836 A1 | 10/2006 |
| WO | WO-2006/111909 A1 | 10/2006 |
| WO | WO-2006/121984 A2 | 11/2006 |
| WO | WO-2006/121984 A3 | 11/2006 |
| WO | WO-2007/148073 A1 | 12/2007 |
| WO | WO-2009/028136 A1 | 3/2009 |
| WO | WO-2010/004365 A1 | 1/2010 |
| WO | WO-2011/084528 A1 | 7/2011 |
| WO | WO-2011/117779 A2 | 9/2011 |
| WO | WO-2011/117779 A3 | 9/2011 |
| WO | WO-2013/160861 A1 | 10/2013 |
| WO | WO-2014/009859 A2 | 1/2014 |
| WO | WO-2014/009859 A3 | 1/2014 |

OTHER PUBLICATIONS

Senarathna et al. "Laser Speckle Contrast Imaging: Theory, Instrumentation and Applications." IEEE Reviews in Biomedical Engineering, vol. 6, 2013, pp. 99-110.*

Briers, J.D. (Nov. 2001). "Laser Doppler, Speckle and Related Techniques for Blood Perfusion Mapping and Imaging," *Physiol. Meas.* 22(4):R35-R66.

Dyck, R.H. et al. (Apr. 1968). "Integrated Arrays of Silicon Photodetectors for Image Sensing," *IEEE Transactions on Electron Devices* 15(4):196-202.

Hillman, E.M. (Sep.-Oct. 2007). "Optical Brain Imaging In Vivo: Techniques and Applications from Animal to Man," *J. Biomed. Opt.* 12(5):051402, total of 49 pages.

Jeong et al. (Feb. 2006). "Functional Optical Coherence Imaging of Tumor Response to a Metabolic Electron Transport Inhibitor," *Proceedings of the SPIE* 6079(1):60790K-1-60790K-8.

Jones, P.B. et al. (Jul.-Aug. 2008). "Simultaneous Multispectral Reflectance Imaging and Laser Speckle Flowmetry of Cerebral Blood Flow and Oxygen Metabolism in Focal Cerebral Ischemia," *J. Biomed Opt.* 13(4):04407, twenty three pages.

(56) References Cited

OTHER PUBLICATIONS

Kalchenko, V. et al. (Feb. 10, 2001). "Multi-modal Diagnostic Approach for Functional Imaging of Tumor Vascular Network and Blood Microcirculation," *Proc. of SPIE* 7898(1):1-7.
Leutenegger, M. et al. (May 9, 2011). "Real-Time Full Field Laser Doppler Imaging," *Biomedical Optics Express* 2(6):1470-1477.
Michelson, G. et al. (Jun. 2002). "Flickering Light Increases Retinal Blood Flow," *Database Biosis [Online] Biosciences Information Service* 22(3):336-343.
Schmeisser, E.T. et al. (May 2003). "Modification of the Heidelberg Retinal Flowmeter to Record Pattern and Flicker Induced Blood Flow Changes", *Documenta Ophthalmologica* 106(3):257-263.
Serov, A. (2002). "Novel Instruments for Remote and Direct-Contact Laser Doppler Perfusion Imaging and Monitoring," Ph.D. Thesis, University of Twente, 128 pages.
Serov, A. et al. (Oct. 3, 2001). "Speckles in Laser Doppler Blood Flowmetry," *Proceedings of the SPIE* 4242:306-318.
Sun, X. et al. (May 14, 2011). "Simultaneous Monitoring of Intracellular PH Changes and Hemodynamic Response During Cortical Spreading Depression by Fluorescence-Corrected Multimodal Optical Imaging," *Neuroimage* 57(3):873-884.
Canadian Notice of Allowance dated Oct. 27, 2017, for Canadian Patent Application No. 2,914,780, filed on Dec. 8, 2015, one page.
Canadian Notice of Allowance dated Sep. 22, 2017, for Canadian Patent Application No. 2,909,914, filed on Oct. 20, 2015, one page.
Canadian Office Action dated Nov. 10, 2016 for Canadian Patent Application No. 2,914,780 filed on Jul. 10, 2012, four pages.
Canadian Office Action dated Oct. 12, 2016 for Canadian Application No. 2,909,914 filed on Apr. 25, 2013, four pages.
European Communication pursuant to Article 94(3) EPC dated Nov. 25, 2016 for European Application No. 08789265.9, filed on Feb. 8, 2011, five pages.
European Communication Pursuant to Rule 164(2)(b) and Article 94(3) EPC dated Jun. 20, 2017, for EP Application No. 11718157.8, filed on Mar. 16, 2011, eight pages.
European Office Action dated Aug. 19, 2008, for EP Application No. 06 744 526.2, filed on Apr. 20, 2006, three pages.
European Office Action dated Dec. 4, 2012, for EP Application No. 06 744 526.2, filed on Apr. 20, 2006, four pages.
European Office Action dated Jul. 1, 2010, for EP Application No. 06 744 526.2, filed on Apr. 20, 2006, five pages.
International Preliminary Report on Patentability (IPRP) (Chapter I) for PCT/IB2008/052787, dated Jan. 11, 2011, ten pages.
International Preliminary Report on Patentability (IPRP) (Chapter I) dated Nov. 16, 2017 for PCT Application No. PCT/CA2016/050526, filed on May 6, 2016, six pages.
International Search and Written Opinion dated Jul. 15, 2016 for PCT Application No. PCT/CA2016/050526, filed on May 6, 2016, eight pages.
International Search Report dated Aug. 14, 2006, for PCT Patent Application No. PCT/IB2006/000940, filed on Apr. 20, 2006, three pages.
International Search Report dated Aug. 14, 2006, for PCT Patent Application No. PCT/IB2006/051167, filed on Apr. 13, 2006, three pages.
International Search Report dated Jan. 3, 2014, for PCT Application No. PCT/IB2013/055517, filed on Jul. 5, 2013, six pages.
International Search Report dated Mar. 24, 2009, for PCT Application No. PCT/IB2008/052787, filed on Jul. 10, 2008, five pages.
International Search Report dated Nov. 23, 2011, for PCT Application No. PCT/IB2011/051098, filed on Mar. 16, 2011, seven pages.
International Search Report dated Sep. 11, 2013, for PCT Application No. PCT/IB2013/053271, filed on Apr. 25, 2013, four pages.
Japanese Notice of Allowance dated Jan. 12, 2018 for Japanese patent Application No. 2016-199363 filed on Oct. 7, 2016, six pages.
Japanese Office Action dated Feb. 1, 2016, for Japanese Patent Application No. 2015-521112, filed Jul. 5, 2013, twelve pages.
Japanese Office Action dated Jul. 7, 2017, for Japanese Application No. 2016-199363, filed on Oct. 7, 2016, eight pages.
Japanese Office Action dated Oct. 30, 2015, for Japanese Patent Application No. 2015-507652, filed on Apr. 25, 2013, nine pages.
U.S. Final Office Action dated Apr. 4, 2016, for U.S. Appl. No. 13/636,268, filed Mar. 4, 2013, thirteen pages.
U.S. Final Office Action dated Aug. 18, 2011, for U.S. Appl. No. 11/912,224, filed Oct. 22, 2007, five pages.
U.S. Final Office Action dated Aug. 23, 2013, for U.S. Appl. No. 13/057,593, filed Mar. 21, 2011, fourteen pages.
U.S. Final Office Action dated Dec. 16, 2016 for U.S. Appl. No. 13/935,947, filed Jul. 5, 2013, twenty three pages.
U.S. Final Office Action dated Feb. 20, 2015, for U.S. Appl. No. 13/636,268, filed Mar. 4, 2013, seventeen pages.
U.S. Final Office Action dated May 19, 2017, for U.S. Appl. No. 14/413,106, filed Jan. 6, 2015, twelve pages.
U.S. Final Office Action dated Nov. 29, 2012, for U.S. Appl. No. 11/912,224, filed Oct. 22, 2007, eight pages.
U.S. Final Office Action dated Oct. 6, 2015, for U.S. Appl. No. 13/935,947, filed Jul. 5, 2013, fifteen pages.
U.S. Final Office Action dated Sep. 26, 2016, for U.S. Appl. No. 13/636,268, filed Mar. 4, 2013, fifteen pages.
U.S. Final Office Action dated Sep. 29, 2017 for U.S. Appl. No. 14/397,290, filed on Oct. 27, 2014, nineteen pages.
U.S. Non Final Office Action dated Jan. 13, 2017 for U.S. Appl. No. 14/397,290, filed on Oct. 27, 2014, thirteen pages.
U.S. Non Final Office Action dated Sep. 29, 2017 for U.S. Appl. No. 13/935,947, filed Jul. 5, 2013, twenty eight pages.
U.S. Non-Final Office Action dated Apr. 29, 2016, for U.S. Appl. No. 13/935,947, filed Jul. 5, 2013, twenty pages.
U.S. Non-Final Office Action dated Aug. 11, 2014, for U.S. Appl. No. 13/057,593, filed Mar. 21, 2011, nineteen pages.
U.S. Non-Final Office Action dated Dec. 17, 2012, for U.S. Appl. No. 13/057,593, filed Mar. 21, 2011, fourteen pages.
U.S. Non-Final Office Action dated Feb. 1, 2017, for U.S. Appl. No. 14/753,997, filed on Jun. 29, 2015, seven pages.
U.S. Non-Final Office Action dated Feb. 14, 2017, for U.S. Appl. No. 13/636,268, filed Mar. 4, 2013, thirteen pages.
U.S. Non-Final Office Action dated Jan. 16, 2015, for U.S. Appl. No. 13/935,947, filed Jul. 5, 2013, seven pages.
U.S. Non-Final Office Action dated Mar. 14, 2012, for U.S. Appl. No. 11/912,224, filed Oct. 22, 2007, seven pages.
U.S. Non-Final Office Action dated Mar. 5, 2018, for U.S. Appl. No. 13/636,268, filed Mar. 4, 2013, seventeen pages.
U.S. Non-Final Office Action dated Mar. 8, 2011, for U.S. Appl. No. 11/912,224, filed Oct. 22, 2007, nine pages.
U.S. Non-Final Office Action dated Nov. 10, 2016, for U.S. Appl. No. 14/413,106, filed Jan. 6, 2015, twelve pages.
U.S. Non-Final Office Action dated Nov. 3, 2015, for U.S. Appl. No. 13/636,268, filed Mar. 4, 2013, fourteen pages.
U.S. Non-Final Office Action dated Sep. 21, 2017, for U.S. Appl. No. 14/413,106, filed Jan. 6, 2015, twelve pages.
U.S. Non-Final Office Action dated Sep. 29, 2014, for U.S. Appl. No. 13/636,268, filed Mar. 4, 2013, ten pages.
U.S. Notice of Allowance dated Feb. 27, 2015, for U.S. Appl. No. 13/057,593, filed Mar. 21, 2011, eight pages.
U.S. Notice of Allowance dated May 5, 2017, for U.S. Appl. No. 14/753,997, filed Jun. 29, 2015, five pages.
U.S. Notice of Allowance dated May 9, 2013, for U.S. Appl. No. 11/912,224, filed Oct. 22, 2007, six pages.
U.S. Supplemental Notice of Allowability dated May 24, 2017, for U.S. Appl. No. 14/753,997, filed Jun. 29, 2015, three pages.
Written Opinion of the International Searching Authority dated Aug. 14, 2006, for PCT Patent Application No. PCT/IB2006/000940, filed on Apr. 20, 2006, seven pages.
Written Opinion of the International Searching Authority dated Aug. 14, 2006, for PCT Patent Application No. PCT/IB2006/051167, filed on Apr. 13, 2006, seven pages.
Written Opinion of the International Searching Authority dated Mar. 24, 2009, for PCT Application No. PCT/IB2008/052787, filed on Jul. 10, 2008, nine pages.

(56) References Cited

OTHER PUBLICATIONS

Written Opinion of the International Searching Authority dated Sep. 11, 2013, for PCT Application No. PCT/IB2013/053271, filed on Apr. 25, 2013, seven pages.
Written Opinion of the International Searching Authority dated Nov. 23, 2011, for PCT Application No. PCT/IB2011/051098, filed on Mar. 16, 2011, ten pages.
Written Opinion of the International Searching Authority dated Jan. 3, 2014, for PCT Application No. PCT/IB2013/055517, filed on Jul. 5, 2013, ten pages.
U.S. Appl. No. 15/663,313, filed Jul. 28, 2017, by Lasser et al.
European Communication pursuant to Article 94(3) EPC dated Mar. 15, 2018 for European Application No. 11718157.8, filed on Mar. 16, 2011, four pages.
U.S. Final Office Action dated Mar. 27, 2018, for U.S. Appl. No. 14/413,106, filed Jan. 6, 2015, thirteen pages.

\* cited by examiner

METHODS AND SYSTEMS FOR LASER SPECKLE IMAGING OF TISSUE USING A COLOR IMAGE SENSOR

CROSS-REFERENCE TO RELATED APPLICATIONS

The application claims priority to U.S. Provisional Patent Application No. 62/158,298, filed May 7, 2015, and titled "METHODS AND SYSTEMS FOR LASER SPECKLE IMAGING OF TISSUE USING A COLOR IMAGE SENSOR," which is hereby incorporated by reference in its entirety.

FIELD

The present disclosure relates generally to the field of medical imaging, and more particularly to laser speckle imaging of tissue using a color image sensor.

BACKGROUND

Laser Speckle Imaging (LSI) may be used to image blood flow and tissue perfusion.

During LSI, the tissue is illuminated using coherent light (e.g., from a laser source), and a speckle image of the tissue is typically acquired using a monochrome image sensor (e.g., CCD or CMOS) with a well-defined exposure time. Due to the coherence of the light used in such imaging, the recorded image contains a speckle pattern. The optical system maps the speckle pattern to the picture elements (pixels) of the image sensor in such a way that each pixel of the image sensor samples a small number of speckles or it oversamples by having a few pixels sampling a single speckle. Typically, near-infrared (NIR) light is used for the illumination due to the reduced opacity of the tissue at these wavelengths. During blood cell movement associated with tissue perfusion, the speckle pattern changes continuously. The exposure time is set such that the speckle pattern changes faster than the exposure time, and thus, the changing speckle pattern becomes blurred. In a spatial-domain approach, the recorded speckle image(s) may be analyzed for contrast by calculating the standard deviation and mean in a kernel around each pixel. In the case of non-perfused tissue (i.e., tissue in which no red blood cells are moving), the speckle pattern has a high contrast because no motion occurs to blur speckles. By applying a non-linear function to each pixel, the contrast image can be subsequently converted into a map of the perfusion state of the tissue. In a time-domain approach, the recorded speckle image(s) may be analyzed for contrast by calculating the standard deviation and mean in a series of image frames for the same pixel. The spatial-domain and time-domain approaches may also be combined. In such a combined approach, the recorded speckle image(s) may be analyzed for contrast by calculating the standard deviation and mean of a series of image frames in a kernel around each pixel.

As an alternative to monochrome image sensors, color image sensors may be used to create monochrome images. Color image sensors may be built using, for example, a Bayer pattern filter in which four pixels forming a square array have one red pixel, two green pixels, and one blue pixel. The acquired raw pixel data filtered through the Bayer pattern may be first converted into a color image using a so-called de-Bayering or demosaicing conversion, and the resulting color image may be subsequently converted into a grayscale/monochrome image. The conversion of the color image to a monochrome image is typically performed by averaging the RGB colors that result from the de-Bayering conversion, sometimes as a weighted average. Although these discrete steps can be combined in a single step, a single pixel in the resulting monochrome image is based on multiple pixels from the color sensor (usually some form of averaging of pixels of the image sensor).

While this conversion of a color image to monochrome image is acceptable for most imaging systems, and often results in reduced noise, such an approach has a negative effect in LSI applications. In LSI, the contrast of the monochrome (speckle) image within a small area may be used to determine perfusion in the tissue. The averaging of multiple pixels when converting a color image to a monochrome speckle image may reduce the contrast and, consequently, reduce the dynamic range of the LSI system and the speckle image quality. The maximum contrast may be reduced, and, thus, a completely static object/non-perfused area of tissue may exhibit a lower contrast than that attainable with a pure monochrome sensor.

Furthermore, in a Bayer pattern color image sensor, although all pixels may be sensitive to near-infrared, this sensitivity is typically not equal for the different color pixels. Therefore, the use of such a color sensor in a system with near-infrared illumination presents an issue because the different sensitivities result in a pattern on the image. Because spatial-domain (or combined time- and spatial-domain) LSI analyzes the contrast within a kernel of several pixels, this pattern may cause an error in the perfusion measurement.

In one approach to addressing this problem, red laser illumination and solely the red pixels of a color sensor can be used to produce a speckle image. However, using only the red pixels of the color sensor to produce the perfusion image limits the utilization of the sensor pixels to only one quarter, which contributes to a reduced resolution of the resultant image. Furthermore, red illumination penetrates less deeply into the tissue compared to near-infrared illumination, and it is not at the isosbestic point of oxy- and deoxyhaemoglobin.

Another drawback of current technologies is that in clinical applications, the speckle image alone lacks contextual information and is noisy due to the speckles; thus, clinical assessment may require a color image. Therefore, to perform clinical assessment, usually a speckle image is linked to a white light image from the same imaging area in order to correlate the perfusion to the corresponding area of the tissue. Currently available technologies either do not produce such a white light image at all, or produce it with a separate image sensor, which may in some instances have the disadvantage of requiring a more complex optical system.

Another drawback of current technologies is the reduction of speckle contrast by ambient light. In LSI, the detection of light other than light from the coherent source may reduce the speckle contrast. This in turn may reduce the quality of the perfusion image.

It is desirable for LSI systems to possess the color image data processing capabilities which maximize the contrast to more accurately represent perfusion, to effectively present speckle images along with white light imaging to the clinician to aid in clinical assessment, and to detect, reduce or eliminate, and/or correct for ambient light.

SUMMARY

In accordance with one aspect of the invention there is provided a method for imaging tissue of a subject. The method includes illuminating the tissue with a coherent light having a coherent wavelength, acquiring image data of the tissue using a color image sensor, and processing the image data using laser speckle contrast analysis while correcting for differences in sensitivity of color pixels at the coherent wavelength to generate a perfusion image of the tissue. The method may further include displaying the perfusion image alone or in combination with other images (e.g., an image showing anatomy of the region of interest).

Correcting for differences in sensitivity of color pixels at the coherent wavelength may include, for example, applying a correction factor to each color pixel. The correction factor may be determined during image data acquisition. Correcting for differences in sensitivity of color pixels at the coherent wavelength may also include changing color channel dependent analog or digital gain of the image sensor. Correcting for differences in sensitivity of color pixels at the coherent wavelength may also include calculating an image for each color pixel (e.g. a contrast image), and using a plurality of the calculated images for each color pixel to calculate the perfusion image.

The coherent light may be alternated between a turned on state and a turned off state during image data acquisition, where the image data acquired during the turned off state of the coherent light includes white light image data to generate a white light image.

In accordance with another aspect of the invention there is provided a method for imaging tissue of a subject where the method involves illuminating the tissue with a coherent light having a coherent wavelength, acquiring image data of the tissue using a color image sensor during a turned on state of the coherent light and during a turned off state of the coherent light, processing the image data comprising pixels of a single color acquired during the turned on state of the coherent light using laser speckle contrast analysis to generate a perfusion image of the tissue, processing image data acquired during the turned off state of the coherent light to generate a white light image. The perfusion image, the white light image or a combination thereof may be displayed to the user. The coherent wavelength may range from about 750 nm to about 850 nm.

In accordance with yet another aspect of the invention, there is provided a system for imaging tissue of a subject. The system includes a coherent light source to generate coherent light having a coherent wavelength, a color image sensor to acquire image data of the tissue, and a processor to process the image data using laser speckle contrast analysis while correcting for differences in sensitivity of color pixels at the coherent wavelength to generate a perfusion image of the tissue. The system may further include a display to display the perfusion image alone or in combination with other images (e.g., an image showing anatomy of the region of interest). Correcting for differences in sensitivity of color pixels at the coherent wavelength may involve applying a correction factor to each color pixel. In another variation, correcting for differences in sensitivity of color pixels at the coherent wavelength may involve changing color channel dependent analog or digital gain of the image sensor. The correction factor may be determined during manufacturing of the system, calibration of the system, use of the system, or a combination thereof. The correction for differences in sensitivity of color pixels at the coherent wavelength may also involve a calculation of an image for each color pixel, and use of a plurality of the calculated images for each color pixel to calculate the perfusion image.

The system may further include a control unit in communication with the color image sensor, the processor, or a combination thereof to control the color image sensor, the processor, the coherent light source, or a combination thereof.

The system may yet further include means to alternate the coherent light between a turned on state and a turned off state during image data acquisition. The image data acquired during the turned off state of the coherent light includes white light image data to generate a white light image. The image data may include ambient light image data, and the processor may further generate an ambient light image.

In accordance with yet another aspect, there is provided a system for imaging tissue of a subject, where the system includes a coherent light source to generate coherent light having a coherent wavelength, wherein the coherent light source has a turned on state and a turned off state, a color image sensor to acquire image data of the tissue during the turned on state and during the turned off state of the coherent light source, a first processor to process the image data comprising pixels of a single color acquired during the turned on state using laser speckle contrast analysis to generate a perfusion image of the tissue, a second processor to process the image data acquired during the turned off state to generate a white light image. The system may also include a display to display the perfusion image, the white light image or a combination thereof to a user.

The system may include a control unit in communication with coherent light source, the color image sensor, the first and second processors, or a combination thereof to control the coherent light source, the color image sensor, the first and second processors, or a combination thereof.

The coherent wavelength may range from about 590 nm to about 750 nm, about 750 nm to about 850 nm, or a combination thereof.

It will be appreciated that the above variations of methods and systems of imaging tissue of a subject can be combined. Two or more of the variations can be combined.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Reference will now be made in detail to implementations and embodiments of various aspects and variations of the invention, examples of which are illustrated in the accompanying drawings.

In this specification, a "white light image" relates to an image acquired under normal white light illumination;

a "speckle image" relates to an image acquired with coherent light illumination;

speckle imaging comprises two processing steps: the first processing step involves a calculation of a spatial and/or temporal contrast, and the second processing step involves a calculation of perfusion from the contrast; in this regard, a "contrast image" relates to an image obtained after the first processing step in speckle imaging, where each pixel represents the speckle contrast (or contrast square) of a kernel of images from the speckle image (for a spatial-domain approach), or the speckle contrast of a pixel over a series of frames (for a time-domain approach), or the speckle contrast of a kernel of images over a series of frames (for a combined spatial- and time-domain approach); and a "perfusion image" relates to a further processed contrast image where the pixel values relate to the perfusion in tissue.

Figure 1:
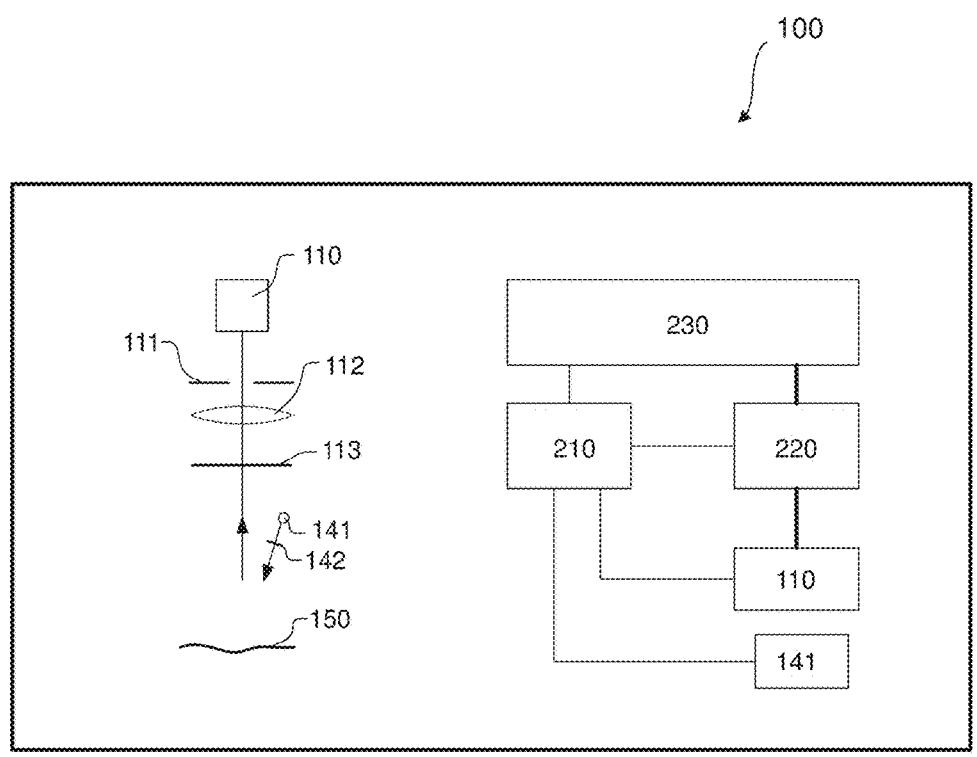
FIG. 1 schematically illustrates an exemplary laser speckle imaging (LSI) system comprising a color image sensor.
Figure 4:
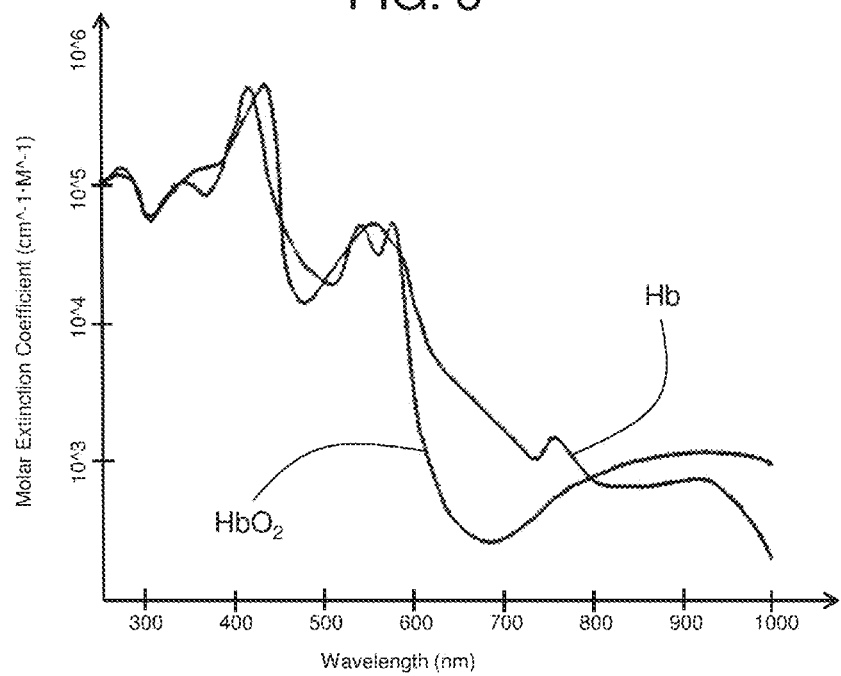
FIG. 4 illustrates absorption curves of oxy- and deoxy-haemoglobin.

Referring to FIG. 1, shown there is an imaging system 100 which may be used, for example, to image tissue perfusion. The imaging system 100 may comprise a coherent light source 141 for illuminating tissue 150 of a subject, an image sensor 110 comprising optical components, a control unit 210, a processing unit 220, and a user interface 230 (e.g., a human-machine-interface "HMI"). In some variations, the coherent light source 141 may include a single-mode laser source at about 800 nm+/− about 50 nm. At this wavelength, the absorption for oxy- and deoxyhaemoglobin (as illustrated in FIG. 4) is substantially equal. It should be appreciated that the coherent light source need not be limited to this wavelength, as long as the image sensor is sensitive to the illumination wavelength.

Optics 142 such as, for example, an engineered diffuser and/or lens system, may be used to shape or otherwise modify illumination of a region on the tissue 150. In some variations, the image sensor 110 may be a CMOS or CCD type color image sensor and may acquire light from the illuminated part of the object or region of interest through a lens or objective 112. A filter 113 (e.g., a long-pass or band-pass filter) may be used to filter light so as to only acquire the wavelength of the coherent illumination source.

In the variation shown in FIG. 1, an aperture 111 may be used to adjust the speckle size on the image sensor 110. The speckle size may be adjusted to optimize the speckle contrast on the image sensor 110.

The control unit 210 may control the image acquisition, and in some variations may pulse coherent light from the coherent light source 141 (e.g., laser). In some variations, the control unit 210 may control or adjust the exposure time of the image sensor 110. The exposure time should be sufficiently long such that the moving speckle pattern blurs the speckle image, but short enough such that the expected moving speeds can be differentiated. In some variations, the exposure time may be in the range of about 1 ms to about 10 ms. These exposure times may be desirable for measuring the perfusion in human skin. Furthermore, the exposure time may be fixed or adjustable depending on the object or region of interest.

The acquired speckle images may be transferred to the processing unit 220, which may calculate the perfusion images. In some variations, the calculation process may include calculating a contrast image and converting the contrast image to a perfusion image. Generally, the contrast image may be converted to a perfusion image by relying on an inversely proportional relationship between the square of the speckle contrast and the flow parameters (e.g., speed, concentration, etc.) of particles (e.g., red blood cells in capillaries). One skilled in the art will appreciate that the systems and methods described herein shall not be limited to the details of the processing algorithm.

The perfusion image may be shown on the user interface 230. The user interface 230 may include, for example, a display and input means such as mouse, keyboard, buttons, or touch screen. In some variations, the sequence of some or all of the optics elements such as the aperture 111, the lens 112, the filter 113, or a combination thereof may be rearranged.

Correcting for Differences in Pixel Sensitivity

Figure 3:
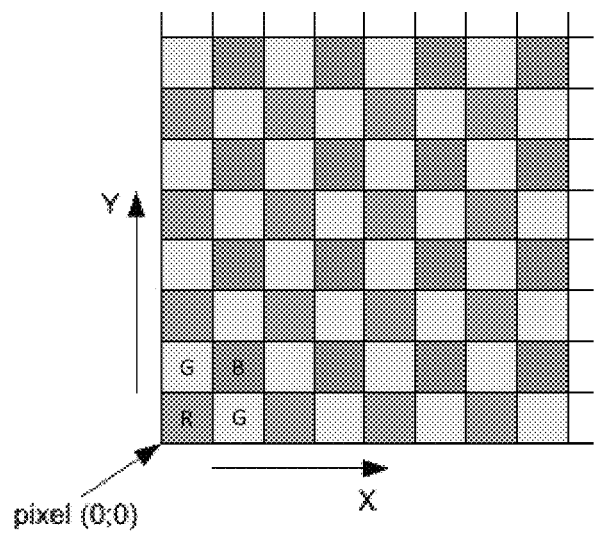
FIG. 3 illustrates a Bayer pattern from an image sensor.

The image sensor 110 may comprise a color sensor (which, in some variations, may include multiple color sensors) to acquire one or more speckle images. A correction may be applied to the speckle image(s) to correct for the influence of the color pixel array (e.g., Bayer pattern, as shown in FIG. 3). In some variations, the correction may be applied, for example, by the sensor, a processor, and/or an algorithm. Color image sensors (e.g., CMOS or CCD) are usually made with, for example, a Bayer pattern filter placed in front of the pixel array. In other variations, other pattern filters may be used including, for example, RGBC, CMYK, or any other pattern filter. The Bayer pattern usually comprises one red, one blue, and two green pixels organized in a two dimensional (2D) array. This array is repeated to form a sensor of the total pixel count. The pixels have a color filter applied to primarily pass the intended wavelength of that color.

Figure 2:
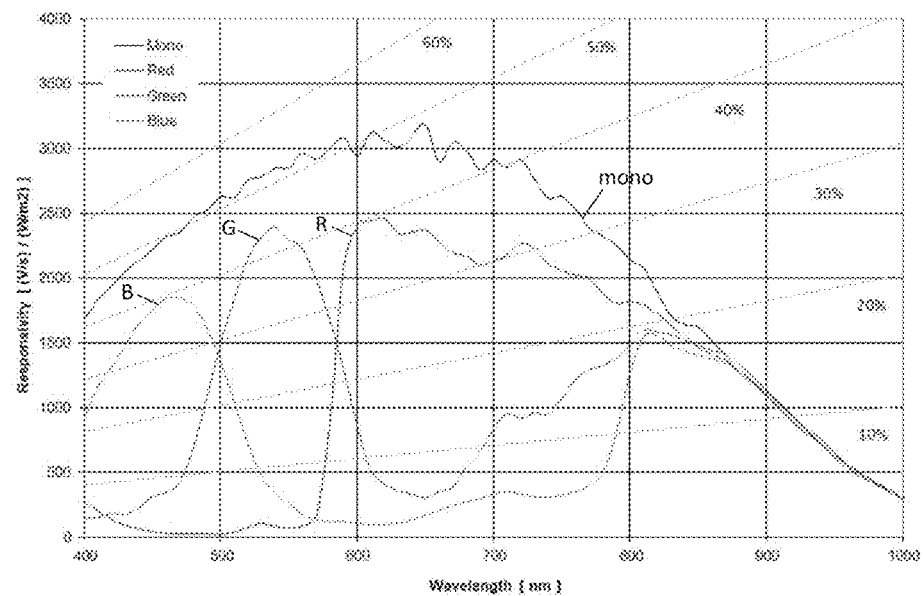
FIG. 2 illustrates example spectra showing different red, green, and blue sensitivities for wavelengths between about 400 nm and 1000 nm for a VITA-1300 image sensor.
Figure 6:
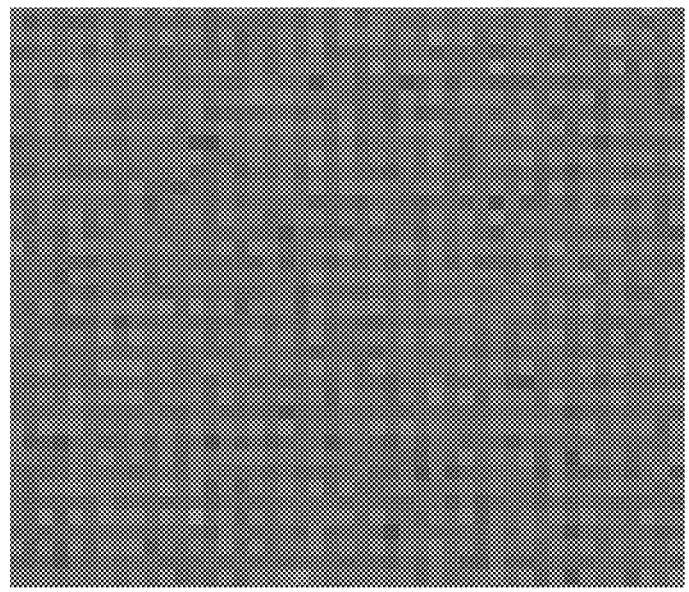
FIG. 6 shows a cropped image of a uniform surface illuminated with non-coherent light and filtered with a long-pass filter only allowing near-infrared light to pass captured with a color sensor.

Usually these color filters also allow through near-infrared or other non-visible light, but sensitivities (spectral responses) of color sensor pixels at those wavelengths are not equal. FIG. 2 shows an example of the spectral responses of a pixel without a filter ("mono"), a red pixel, a green pixel, and a blue pixel. As shown there, all four types of pixels can generally detect light in the near-infrared portion of the spectrum, but the spectral response across these wavelengths differs for each type of pixel. Consequently, when using the raw sensor data from an image sensor 110 comprising a Bayer pattern filter to image an object which is primarily illuminated with near-infrared light, the Bayer filter appears as a pattern on the image. An example of this effect is illustrated in FIG. 6. As can be seen there, the structure of the Bayer pattern is visible in the image.

Figure 5A:
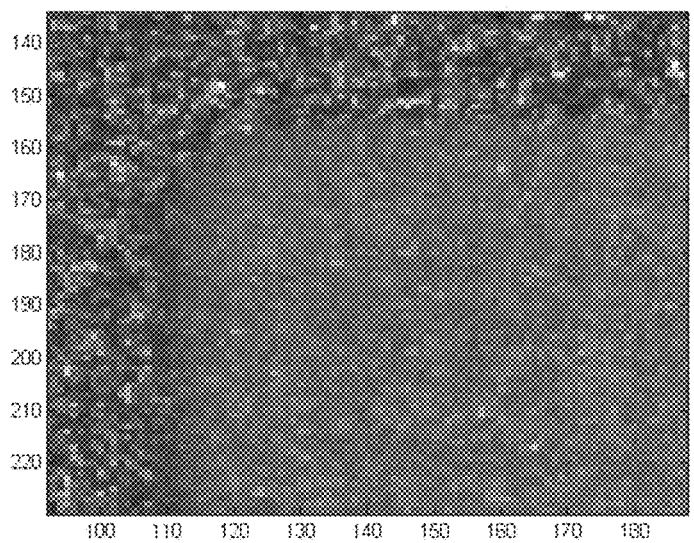
FIGS. 5A-5B illustrate a comparison of a speckle pattern of a moving surface on a test bench with a monochrome sensor (FIG. 5A) and a color (FIG. 5B) sensor.
Figure 5B:
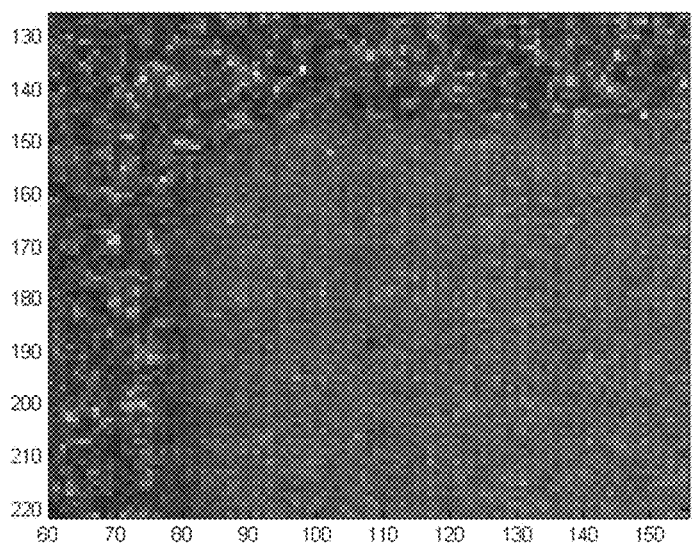

Because a spatial-domain (or combined spatial- and time-domain) LSI algorithm typically works by analyzing the spatial contrast in an image, such an image sensor having a color pixel array (e.g., a Bayer pattern filter) may cause a measurement error in the detected motion of an imaged object. A comparison of FIGS. 5A and 5B illustrates this effect. FIGS. 5A and 5B are speckle images of a moving object generated using a monochrome sensor and a color sensor, respectively, of the same sensor family. In each figure, the top left border corresponds to a non-moving portion of a test bench. In FIG. 5B, the portion of the image corresponding to a moving portion of the test bench shows increased contrast (relative to the same image portion in FIG. 5A) due to the Bayer pattern of the sensor (more specifically, increased spatial contrast due to different sensitivities of RBG pixels). The speckle image may always have some contrast due to the Bayer pattern, and thus, the algorithm may not be able to separate between faster moving speeds. While the influence is certainly reduced in pure time-domain algorithms, different sensitivity might still have some influence.

Figure 9:
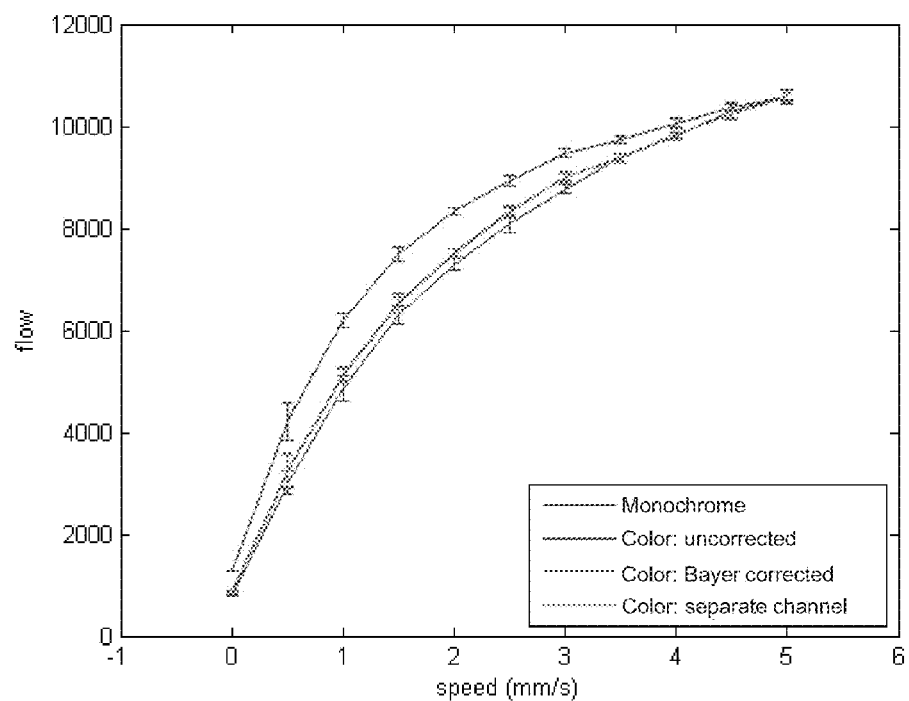
FIG. 9 compares perfusion values, determined in different manners, for a test bench object moving at different speeds.

This effect is also visible in FIG. 9. FIG. 9 shows effective perfusion value measurements when imaging a moving object at different speeds on a test bench, using a monochrome sensor and using a color sensor. The speed to perfusion values are scaled to show the same result at 5 mm/s. The slope of perfusion measurements from the uncorrected color camera shows that high-speed movements may not be able to be distinguished.

Correction Factors

Described herein are different approaches that may be used to correct images acquired using a sensor comprising a color pixel array (e.g., having a Bayer pattern) for LSI applications. These approaches may correct for differences in sensitivity of color pixels at the coherent wavelength. In a first approach, the effect of the different sensitivities of pixels may be corrected by applying a linear or non-linear correction to each pixel. The applied correction may be different for each color of pixel (i.e., for pixels with different color filters above the pixels). In some variations, the correction may comprise multiplication by a multiplying factor. In other variations, the correction may comprise another form of correction factor (e.g., a linear or non-linear function). For simplicity, whenever "correction factor" is used herein, it may be a multiplying factor or any other form of correction, whether linear or non-linear.

In some variations, for example, three correction factors may be used for a sensor having a Bayer filter: one for all the red pixels, one for all the green pixels, and one for all the blue pixels in the array. In other variations, for example, four correction factors may be used for a sensor having a Bayer filter: one for all the red pixels, one for all the blue pixels, and two different correction factors for the green pixels. This may be desirable because in the Bayer pattern, the two green pixels may have slightly different spectral responses, and as such, a different correction factor for each of the two green pixels may be used. In other (non-Bayer) color pixel array pattern types, more or fewer correction factors may be used based on the different filters applied to the pixels. The correction factors may also be different for each individual sensor or for a combination of sensors.

In some variations, one or more of the correction factors for a particular sensor may be determined theoretically. In other variations, one or more of the correction factors for a particular sensor may be determined experimentally, for example, by imaging a uniform object or target that is illuminated with non-coherent light (i.e., light that will not result in speckles in an image) at the same wavelength as the coherent light source to be used in LSI with the sensor. The mean values of all color pixels in the image of the uniform object or target may then be calculated. When the correction factor is a multiplying factor, the multiplying factor for each pixel may then be chosen such that after multiplying each pixel value by the multiplying factor for that color, the resulting image is a uniform image (i.e., where each pixel has the same value). This step can be performed, for example, once during manufacturing of the system, at regular intervals, or continuously (e.g., during or before each image capture). In some variations, time-domain filters can be applied to reduce any short-term effects.

Figure 7:
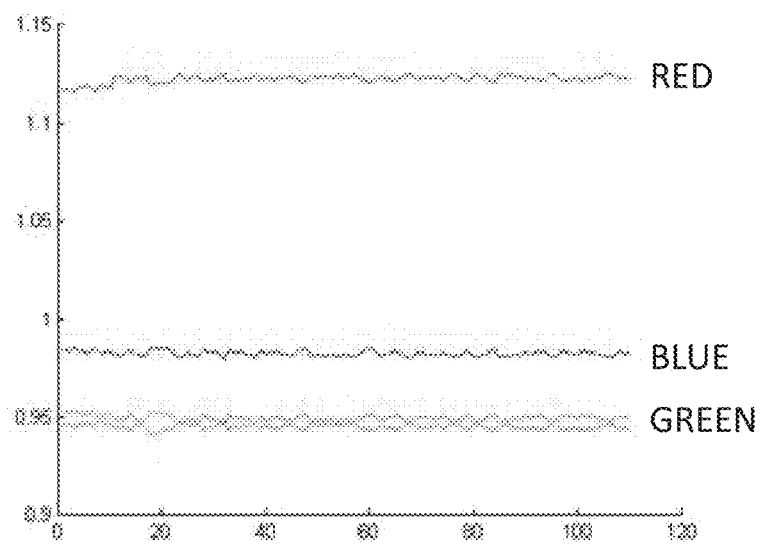
FIG. 7 is a graph illustrating the detected pattern for each frame (about 110 frames) in connection with the exemplary color sensor correction methods described herein.

It should be appreciated that in other variations, the imaged object may be non-uniform, and/or the illumination may be coherent with resulting speckles in an image. If the image resolution is acceptable as compared to the imaged structure and the image resolution (number of pixels) is high enough, the relationship of the mean values of the different color pixels of such an image may remain mostly constant for all images, and thus the mean values of all pixels may be used to determine correction factors. FIG. 7 shows exemplary correction factors for a Bayer-type image sensor determined from a 110-frame recording of a hand, where the correction factor is determined from each frame individually. The curves show a good stability of the detection of the correction factors across frames. Optionally, correction factor accuracy may be further improved by time-domain filtering.

In some variations, the correction factors for a sensor may be statistically maintained over time. In some of these variations, there may be a pre-determined set of correction factors. The correction factors may then be updated over time based on previous and/or current images.

After correction of the acquired speckle images using one or more correction factors, as described herein, the image may be processed using an LSI algorithm to determine perfusion measurements.

Channel-Specific Settings

In another variation of an approach to correcting for differences in sensitivity of color pixels at the coherent wavelength, the image sensor may be configured to allow different analog or digital gain settings for each color channel. The gain may include, for example, a multiplication factor (and, in some variations, an offset value). With such a sensor, the relationship between the number of detected photons and the signal output may be adjusted for each color channel separately. A control unit of the imaging system may set this gain such that it applies a correction factor for each color channel. Thus, in these variations, the correction for different pixel sensitivities at the coherent wavelength may be done within the image sensor using adjusted color-dependent gain, rather than during subsequent processing. The correction factors may be fixed or static, or one or more of the correction factors may be updated over time. In the latter method, the gain settings of the sensor may be updated whenever a new set of correction factors is determined.

In another variation of an approach to correcting for differences in sensitivity of color pixels at the coherent wavelength, correction may be partially done using channel-specific gain settings as described herein, and partially by processing (e.g., with correction factors). An example includes using a gain from the sensor, but adding an offset in processing. Similarly, the sensor may additionally or alternatively be configured to allow the adding or subtracting of different offset values from the signal output for different color channels in order to correct the images (e.g. having a blacklevel adjustment based on color channel).

Separate LSI Processing

In some variations, correction for differences in sensitivity of color pixels at the coherent wavelength may not be applied to the acquired image, but rather the LSI algorithm or part of it may be performed on each color channel individually. For instance, a spatial-domain LSI algorithm may analyze the spatial contrast separately for each color channel of the sensor. Thus, for example, in cases in which a classic Bayer pattern with an array of four pixels is used, the LSI algorithm may be processed four times, once for each of the four types of color pixel in the array. The resulting four perfusion images may then be averaged or otherwise combined to result in a single perfusion image. Calculating the perfusion separately for each color channel in this way may avoid the need to apply correction factors to the pixel values prior to applying an LSI algorithm to determine perfusion, since the different color pixels, with their differing sensitivities to the illumination light (e.g., coherent near-infrared illumination), are analyzed separately. In this variation, typically, the kernel size used for spatial-domain LSI on each separate color channel may be smaller to compensate for the reduced image resolution of each single LSI image (i.e., an LSI image generated from a single pixel color), but the combination of the multiple LSI images may compensate for the increased noise due to the smaller kernel size. It should be appreciated that in some variations, the algorithm need not perform the full LSI algorithm to generate a perfusion image for each color channel. For example, the channels could be combined at other steps in the algorithm such as, for example, after calculation of the contrast images.

Figure 8A:
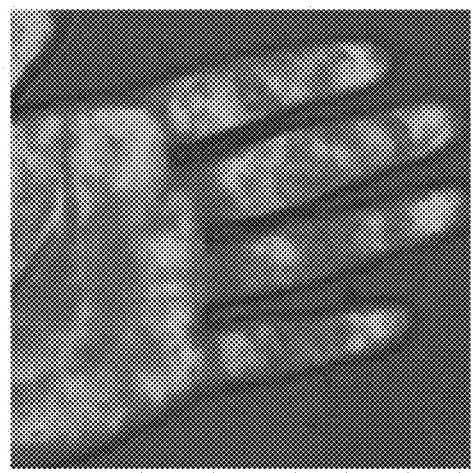
FIGS. 8A-8C illustrate an uncorrected processed image (FIG. 8A), a separate channel processed image (FIG. 8B), and a Bayer corrected processed image (FIG. 8C)
Figure 8B:
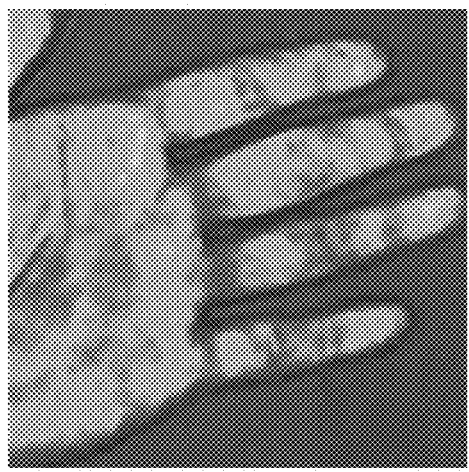
Figure 8C:

FIGS. 7, 8, and 9 illustrate data relating to examples of approaches to correcting for differences in sensitivity of color pixels of image sensors at the coherent wavelength. The same raw input data from a recording of a hand was used for all algorithms. In one method a correction factor was applied to each color channel prior to applying the LSI algorithm (referred to as the Bayer corrected method), see FIG. 8C. In another method the perfusion image was generated with an LSI processing algorithm, where the LSI algorithm was applied separately to each color channel from the image sensor, without application of a correction factor prior to applying the LSI algorithm. After the LSI algorithm was applied separately to each color channel to generate four perfusion images, the four perfusion images were averaged to generate the single perfusion image shown FIG. 8B. For comparison, the data was processed without any correction, see FIG. 8A.

For the Bayer corrected method, two methods were tested to determine the multiplying factor. In one method, all the raw images were processed to find a fixed multiplying factor. In another method, only the current frame was used to determine the multiplying factor. FIG. 7 is a graph illustrating the method in which the current frame is used to determine the multiplying factors. The graph shows the determined correction factors for a Bayer-type image sensor for each frame (about 110 frames) of the recording of a hand. As can be seen there, the correction factors determined for each frame are approximately the same. Consequently, no visible difference was seen between the two methods of determining the multiplying factor. Also the test bench curve showed substantially no difference between the two methods. In some variations, an on-going process may be used to find the correction pattern, and it may be possible to detect the pattern on the frame.

The methods were further compared on the test bench. The data in FIG. 9 illustrates that the Bayer-corrected (FIG. 8C) and the separate-channel processed (FIG. 8B) procedures show comparable results, which are similar to the results using a monochrome image sensor. Although there may be some minimal difference between the results obtained from the monochrome sensor and the Bayer-corrected (FIG. 8C) and separate-channel (FIG. 8B) approaches, such a difference does not appear to be clinically visually perceptible. In contrast, FIG. 9 shows that the uncorrected results (FIG. 8A) are significantly different from the monochrome, Bayer-corrected, and separate-channel results.

The methods and systems described herein are applicable to any sensors having a pattern of color pixels. For example, the methods and systems are applicable to non-classical Bayer pattern image sensors such as, for example, sensors that have other distributions of color filters on pixels or other color filters. The description herein of the various embodiments in connection with the Bayer pattern is applicable and may be adapted to any other specific pattern. In this specification, a "color pixel" relates to a pixel that primarily detects the light a of specific wavelength range, independent of the actual implementation. While the implementation for a conventional color sensor is done with a color filter above the pixel, the methods and systems described herein apply to all types of color sensors that are made of an array of pixels sensing different colors, where all pixels may be somewhat sensitive to the coherent wavelength (e.g., all color sensors having color mosaic filters which become approximately transparent in the NIR and not having an NIR cutoff filter) independent of the actual implementation.

Light Source and Sensor Types

In some variations, it may be possible to additionally or alternatively reduce unwanted effects from sensor pixel patterns by choosing a coherent light source and image sensor such that the image sensor is sufficiently equally sensitive to the coherent light source wavelength for all pixels. In these variations, methods for correcting for differences in sensitivity of color pixels at the coherent wavelength as described herein may not be needed.

For example, in some Bayer-type image sensors, the red, blue, and both green pixels may have equal sensitivity above about 830 nm. The wavelength threshold above which all sensor pixels are sufficiently equally sensitive may vary by sensor type and sensor calibration. FIG. 2 shows an example of an image sensor having red, green, and blue pixels. As shown there, all three pixel types are approximately equally sensitive above 860 nm. Thus, a coherent light source for use with this sensor may be chosen between about 825 nm to about 900 nm. Wavelengths in this range may provide good penetration depth into tissue while also resulting in a sufficiently equal response on all color pixels. It should be appreciated that such image sensors are not limited to Bayer-type sensors and may have any suitable pixel pattern.

Reducing Unwanted Effects from Ambient Light

Also described herein are systems and methods for reducing unwanted effects of ambient light (i.e., non-coherent light) in LSI. In LSI, the detection of light other than light from the coherent source may reduce the speckle contrast. This in turn may reduce the quality of the perfusion image. Therefore, some variations of systems described herein may be configured to detect, reduce or eliminate, and/or correct for ambient light.

Reduce Ambient Light

In some variations, unwanted effects of ambient light may be reduced, for example, by filtering the light reaching the laser speckle image sensor. For example, in the variation shown in FIG. 1, the filter 113 (e.g., band-pass or long-pass filter) may only pass the wavelength of the coherent light source 141. For example, a 780 nm long-pass filter may be used if the coherent light source 141 is at about 808 nm. Filter 1113 in FIG. 11 may similarly only pass the wavelength of the coherent light source 1141. As the majority of image sensors are not sensitive to or have a reduced sensitivity to light having wavelengths above about 900 nm, in some variations, a long-pass filter may be sufficient and a band-pass filter may not be needed. Having such ambient light filters may reduce the ambient light outside the coherence light source wavelengths from reaching the laser speckle image sensor.

Detect and/or Correct for Ambient Light

Additionally or alternatively to optically filtering out ambient light (e.g., using filter 113 or 1113), the systems described herein may detect and/or correct for ambient light reaching the laser speckle image sensor. When no ambient light filter as described above is employed, the image sensor may receive ambient light, including visible ambient light and ambient light in the coherent light source wavelengths. Even when an ambient light filter is employed as described above, ambient light within the coherent light source wavelengths (e.g., near-infrared light) may still reach the laser speckle image sensor.

The ambient light may be detected using any suitable method, such as the methods described herein, including using the laser speckle image sensor, a dedicated ambient light sensor, and/or a white light image sensor. Once detected, the laser speckle image may be corrected for the ambient light. Additionally or alternatively, the system may be configured to warn a user about the presence of ambient light. For example, if the ambient image meets a particular threshold, the system may be configured to warn the user about ambient light conditions that may affect the accuracy of the LSI.

Using a Laser Speckle Image Sensor

In some variations, the systems described herein may correct or compensate for ambient light using the laser speckle image sensor. Correction for ambient light may be done by, for example, repeatedly switching on and off the coherent light source. This may be done using a control unit such as control unit 210 in FIG. 1. The control unit may permit collecting at least one image frame from the laser speckle image sensor without coherent light, which shall be referred to as the ambient image. This ambient image may then be used to determine the ambient light condition. This information may be used to subtract the ambient light from a speckle image. In some variations, for example, the ambient image may be subtracted from each acquired speckle image. The ambient image may optionally be acquired with different sensor settings such as, for example, different exposure time or gain. In such a case, the ambient image may be processed to account for the different sensor settings (e.g., by multiplying each pixel value by a factor) before it is subtracted from the speckle image. The frequency of taking the ambient image may depend on the application. In many medical applications, the ambient image may be acquired at the frame rate of the speckle image or at least once every second. The speckle images corrected for ambient light may then be processed by the LSI algorithm using a processing unit (e.g., processing unit 220 of FIG. 1).

In other variations, the laser speckle image sensor (e.g., laser speckle image sensor 110 of FIG. 1) may have a larger field of view than the area illuminated by the coherent light source (e.g., coherent light source 141 of FIG. 1). The area outside the illumination area may not be used to produce a speckle image, but rather to detect ambient light. The amount of light in that area during laser speckle imaging may correspond to the disturbing ambient light and may be used to correct the speckle image.

Using a Separate Ambient Light Sensor

The systems described here may additionally or alternatively comprise a dedicated ambient light sensor (i.e., separate from an image sensor used to acquire a speckle image or a white light image). The ambient light sensor may comprise a single pixel, a small pixel array, or a full image sensor to detect ambient light. The ambient light sensor may further comprise lenses or other optical elements to image a target area to the sensing electronics.

The ambient light sensor may in some instances be configured to measure ambient light within the wavelength ranges of the coherent light source. For example, when the coherent light source provides illumination in near-infrared wavelengths, the ambient light sensor may be configured to measure near-infrared ambient light. In some variations, the ambient light sensor may be an RGBW sensor (also known as a W-RBG sensor) or an RGBIR sensor (also known as an IR-RGB sensor). These sensors may comprise a filter having a modified Bayer pattern that replaces a green pixel with a white (i.e., wide wavelength range) or infrared pixel. Thus, these types of sensors may be used to differentiate near-infrared and visible ambient light. In other variations, the ambient light sensor may comprise a long-pass or band-pass filter (similar or the same as filter 113 used in front of the laser speckle image sensor 110 in FIG. 1) to limit the light reaching the sensor to light in the wavelength range of the coherent light source.

In some variations, the ambient light sensor may be positioned such that it measures the ambient light within the area illuminated by the coherent light source. In these variations, the coherent light source may be switched on and off, and the ambient light sensor may be controlled such that it detects the disturbing ambient light during the switched off phase. In other variations, the ambient light sensor may be positioned such that it measures the ambient light close to, but outside, the area illuminated by the coherent light source. In these variations, it may generally be assumed that such ambient light is representative of the ambient light in the area illuminated by the coherent light source.

Using a White Light Image Sensor

In systems comprising a white light image sensor, the white light image sensor may additionally or alternatively be used to detect and/or correct for ambient light. For example, a white light image sensor (e.g., white light image sensor 1120 in FIGS. 11A-11C) may be configured to have a larger field of view than the white light illumination area. The amount of light detected on the area outside the white light illumination area may be used to determine the disturbing ambient light.

It should be appreciated that ambient light detection or compensation as described herein may be used in conjunction with a wavelength filter configured to only pass the wavelength of the coherent light source as described herein. This may allow for correction for ambient light having the same wavelengths as the coherent light source. This may be relevant, for example, if the coherent light is in the visible range. This may also be relevant if the coherent light is in the near-infrared wavelength because some ambient light (such as sunlight or strong operating room light) may contain near-infrared light.

It should further be appreciated that the ambient light reduction, detection, and/or correction techniques described herein with respect to laser speckle imaging using a color image sensor are more broadly applicable and may, for example, also be use with systems and methods using a monochrome image sensor for laser speckle imaging.

Acquisition of a White Light Image

In some variations of LSI, such as in some clinical applications, it may be desirable to acquire a white light color image from the same or similar surface and at the same or similar time as a speckle image.

Acquisition with the Same Sensor

In some variations, the methods and systems described herein may use the same color image sensor for both white light and laser speckle imaging.

In some of these variations, this may be carried out by switching the coherent light source on and off. For example, turning back to FIG. 1, in some variations a white light image may be acquired with the same image sensor 110 as the speckle image. In some of these variations no filter 113 is located between the tissue 150 and image sensor 110, while in other variations, the system may comprise a filter 113 (e.g., a band-pass or long-pass filter) configured to pass at least most of the visible light and the coherent light. The control unit 210 may switch the coherent light source 141 on/off repeatedly. Synchronized with the switching on/off of the coherent light source, the control unit may also function to adjust acquisition parameters of the image sensor 110, such as the exposure time and gain of the image sensor 110. Adjusting these parameters during acquisition of the white light image may improve image quality when the white light illumination is significantly weaker than the coherent light illumination. In these cases, the exposure time of the image sensor 110 for LSI using the coherent light source may be too short to acquire reasonable white light images at normal light conditions.

The image sensor may comprise any suitable color image sensor. The sensor in some variations may comprise a Bayer-type sensor. In other variations, the image sensor may comprise an RGBW sensor (also known as a W-RBG sensor), an RGBIR sensor (also known as an IR-RGB sensor), or a similar type of sensor. These sensors comprise a filter having a modified Bayer pattern that replaces a green pixel with a white (i.e., wide wavelength range) or infrared pixel. When the image sensor is an RGBW or RGBIR sensor or the like, the white light and speckle images may be acquired by switching the coherent light source on and off, as described above. This may be advantageous because it may allow for detection and/or correction for ambient light, as described herein.

Figure 10A:
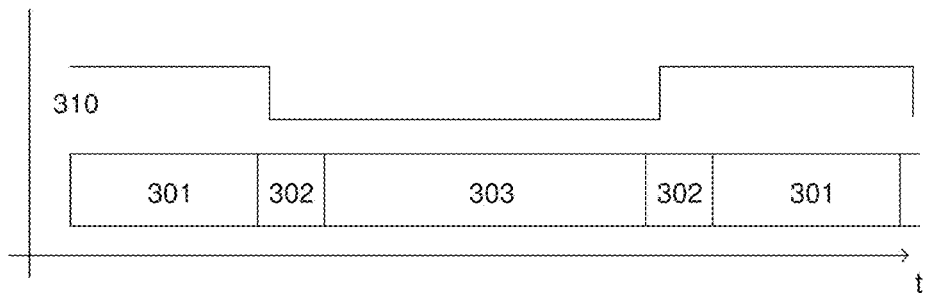
FIGS. 10A and 10B illustrate two exemplary control sequences for white light image acquisition and speckle image acquisition using the same sensor.
Figure 10B:
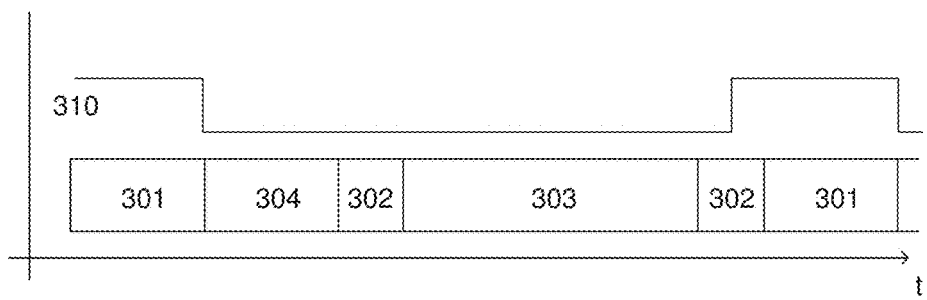

FIGS. 10A and 10B show example sequences of such alternating image acquisition. The coherent light control line is shown in 310. In the variation shown in FIG. 10A, the coherent light control may be enabled (i.e., the coherent light may be on) during the speckle image acquisition 301 and disabled (i.e., the coherent light may be off) during the white light image acquisition 303. Between acquisitions of the images, the sensor may be reconfigured over time period 302. The acquisition/exposure times of the two modes 301 and 303 may be different. Other sequences may also include, for example, multiple acquisitions of one acquisition mode (e.g. speckle image) and then a single or multiple frame of the other mode (e.g., white light mode).

In some variations, the full image sensor (i.e., all of the pixels) may be used to generate the speckle image. In these variations, the distortion of the speckle image due to the pattern of the color image sensor (e.g., a Bayer pattern) may be corrected using one of the methods described herein. The speckle image may also be corrected to reduce the effects of ambient light using the methods described herein. In some instances the acquisition of an ambient light image may be simultaneous with acquisition of the white light image (i.e., it is the same image data as the white light image), while in other instances an ambient light image may be acquired separately from the white light image, as described in more detail herein. In these instances, the acquisition sequence may contain a separate time period 304 (as shown in FIG. 10B) to acquire the ambient light image. This may be preferable in cases where the ambient image is acquired with the same sensor configuration as the speckle image.

In other variations, a subset of the sensor pixels may be used for the speckle image. That is, instead of using the full image sensor to generate the speckle image, only a single color channel of the sensor may be used. In these variations, the speckle image may have less resolution than the color image, since it uses only a subset of the sensor's pixels. For example, only the red pixels may be used to produce the speckle image. In this example, the coherent light source may preferably be chosen to have wavelengths in the visible range, such as in red, but this variation may work with coherent light sources that produce near-infrared light as well. As another example, where an RGBW or RGBIR image sensor is used for both white light imaging and speckle imaging, only the white or infrared color channel of the image sensor may be used to generate the speckle image. In this example, the coherent light source may preferably be chosen to have wavelengths in the near-infrared range.

Figure 13:
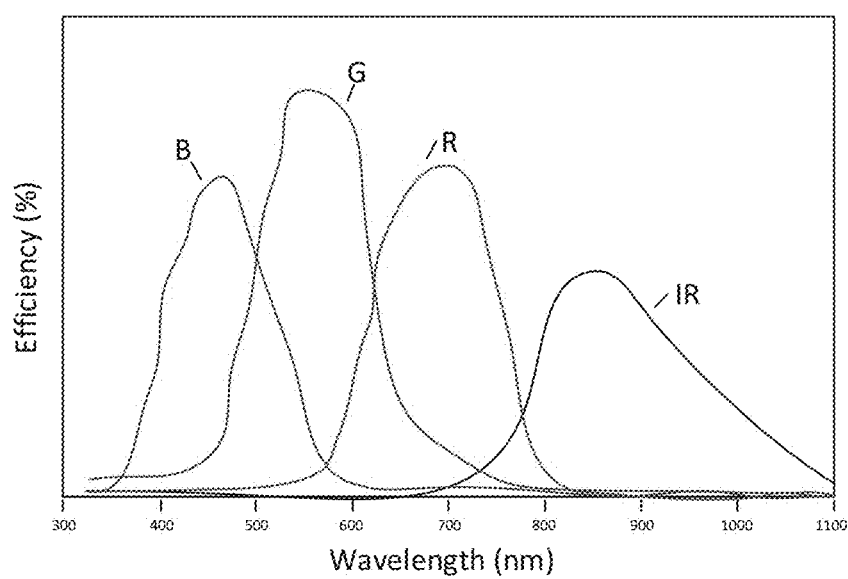
FIG. 13 illustrates an exemplary spectral response of a modified RGBIR image sensor.

In other variations, the sensor may be used to acquire the white light and speckle images without switching the coherent light source on and off. The white light and speckle images may be acquired simultaneously, and a single exposure may provide both images. For example, the sensor may comprise a modified RGBW or RGBIR sensor. The sensors may be modified to reduce the sensitivity of the red, green, and blue pixels to near-infrared light. An example of such a sensor, a modified RGBIR sensor, is shown in FIG. 13. As shown there, the sensor may have no or very little sensitivity to near-infrared light for the red, green, and blue pixels, while the infrared pixel (or the white pixel in the case of an RGBW sensor) may be sensitive to near-infrared light. The red, green, and blue color channels may be used to generate the white light image, while the white (in the case of an RGBW sensor) or the infrared (in the case of an RGBIR sensor) pixel may be used to generate the speckle image from a near-infrared coherent light source. When the sensor is an RGBW sensor, the white pixels may be further corrected for ambient light using the neighboring RGB pixel values. In these variations, no band-pass or long-pass filter may be needed between the tissue and the image sensor, since it may be desirable that visible and coherent light reach the image sensor.

In yet other variations in which the same color image sensor is used to acquire white light and speckle images, the filter 113 located between the tissue and image sensor may be configured such that it can be enabled or disabled by the control unit 220. The coherent light source may use a wavelength in the non-visible range such as in the near-infrared. The filter may be controlled to enable or disable passing the visible light to the image sensor. Such a configuration may include mechanical parts for moving the filter or opto-electrical components. The filter may be controlled such that it allows passing of the visible light when the white light image is acquired, and it blocks the visible light during the acquisition of the speckle image. In such an embodiment, the ambient light correction does not necessarily need to be performed.

Acquisition with a Different Sensor

Figure 11A:
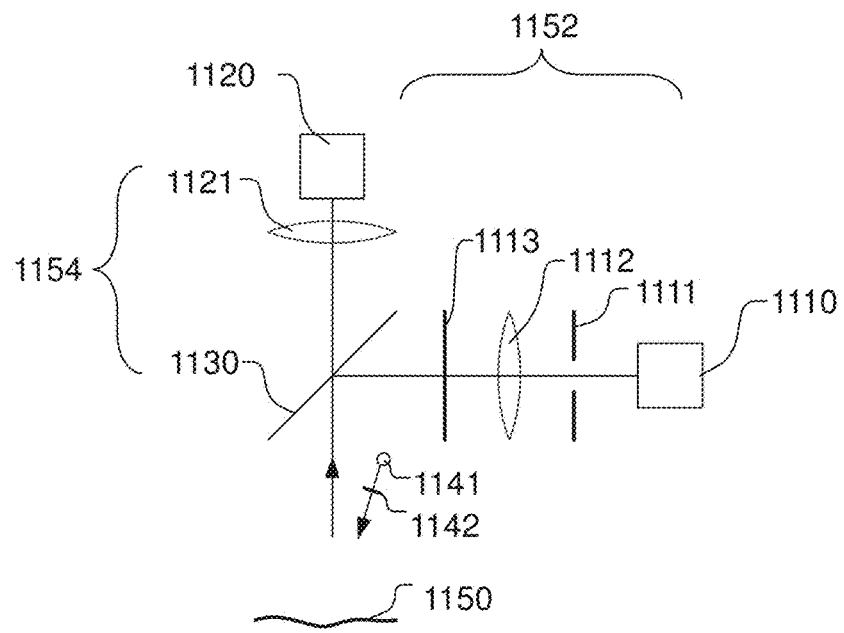
FIGS. 11A and 11B illustrate two exemplary optical setups with two separate image sensors for white light image acquisition and speckle image acquisition.
Figure 11B:
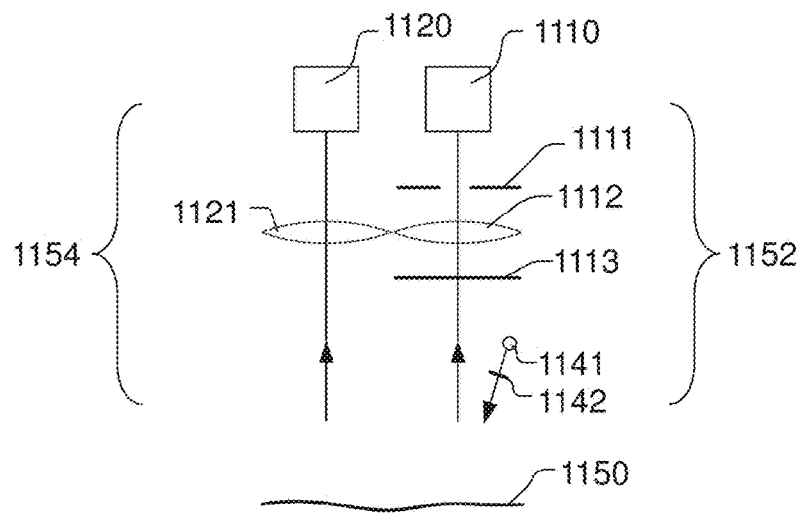
Figure 11C:
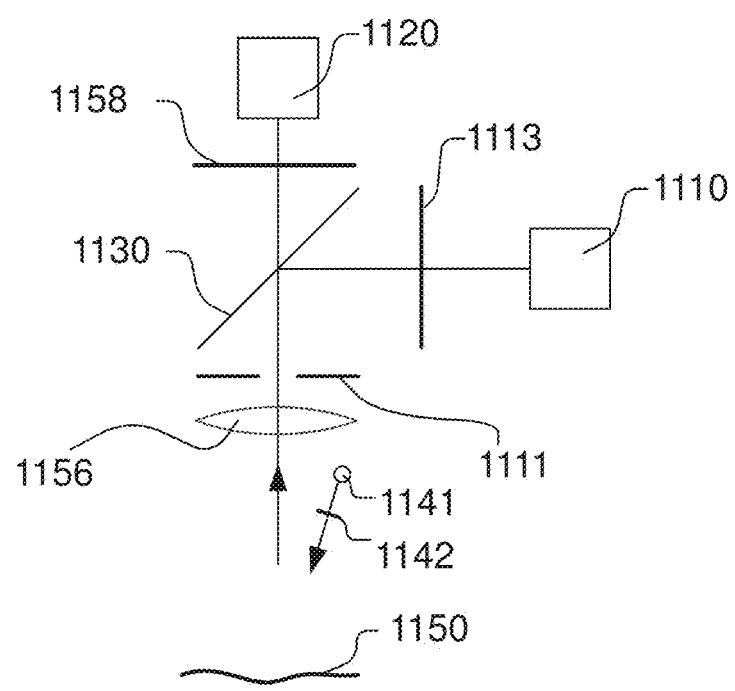
FIG. 11C shows another exemplary optical setup with two separate image sensors for white light image acquisition and speckle image acquisition.

In other variations, the white light image may be acquired with a different image sensor than the image sensor used to acquire the laser speckle image. FIGS. 11A-11C show examples of imaging systems having separate image sensors for white light and speckle images. It should be appreciated that in these variations, the laser speckle image sensor may comprise a color image sensor (e.g., any of the color image sensors described herein, such as a Bayer-type sensor, an RGBW sensor, an RGBIR sensor, or the like), or it may comprise a monochrome sensor.

Referring to FIG. 11A, the two image sensors 1110 and 1120 partially share an optical path. A beam splitter 1130 such as, for example, a dichroic mirror may split light returning from the tissue 1150 into a laser speckle imaging path 1152 and a white light imaging path 1154.

The beam splitter 1130 passes the majority of light at the wavelength of the coherent light source to the laser speckle imaging path 1152. As shown in FIG. 11A, a filter 1113 (e.g., a long-pass or band-pass filter), lens system 1112, and aperture 1111 may be implemented in this path 1152. In some variations the filter 1113 may be omitted because, for example, the beam splitter 1130 is also configured as a filter, or because ambient light correction is implemented, as described in more detail herein. The image sensor 1110 (laser speckle image sensor) may be a color image sensor and may be configured for controlled exposure time as described herein.

In some variations in which separate laser speckle and white light image sensors are used, linear polarization in the laser speckle imaging path may be implemented. For example, a linear polarizing filter may be implemented in the imaging path of the laser speckle image sensor. As another example, the linear polarization may be implemented using a polarizing beam splitter (or polarizing beam splitter cube) for the beam splitter (e.g., beam splitter 1130). In these examples, a long-pass or band-pass filter 1113 may be implemented before the laser speckle image sensor (e.g., laser speckle image sensor 1110).

Most of the visible light may be directed to the image sensor 1120 (white light image sensor) by the beam splitter 1130. A separate lens system 1121 (which may also function as a filter) and/or an aperture (not shown) may be integrated in the path 1154. Typically, a CMOS or CCD color sensor may be used for the white light image sensor 1120. As described in connection with FIG. 1, the illumination light may be generated by the coherent light source 1141 (e.g., a laser) and optics comprising a beam expander 1142 (e.g., an engineered diffuser and/or lens system).

Both image sensors 1110 and 1120 may be connected to a control unit and a processing unit, such as the control unit 220 and processing unit 230 described with respect to FIG. 1. The control unit may control the acquisition of images by the image sensors 1110 and 1120. The processing unit may process the laser speckle image and generate the perfusion image, or in other variations, the processing may be performed by separate processing units. The data from the white light image sensor 1120 may be processed to produce a color image. In some variations, the images may be scaled to match each other.

In other variations, the white light and speckle image sensors may have separate optical paths. For example, in the variation illustrated in FIG. 11B, the image sensors 1110 and 1120 may be arranged substantially in parallel or with a small angle between them, such that each sensor may have a separate optical path, without a beam splitter. It may be preferable that the optical paths are very close, as this may minimize the distortion and/or offset of the images. The one or more processing units used to produce the perfusion and color images may be configured to correct one or both of the images to compensate for any distortion and/or offset.

It should be appreciated that the optical elements of the systems described herein need not be arranged in the order shown in FIGS. 11A and 11B, and may have other suitable arrangements. For example, FIG. 11C illustrates a system comprising a beam splitter (such that the two image sensors 1110 and 1120 share a portion of their optical paths), with an arrangement such that light from the tissue 1150 passes through one or more optical elements before reaching the beam splitter. As shown there, light returning from the tissue 1150 may pass through an objective lens system 1156 and aperture 1111 prior to reaching the beam splitter 1130. A portion of the light may be reflected by the beam splitter 1130 and travel through a filter 1113 (e.g., a long-pass or band-pass filter) to an image sensor 1110 (laser speckle image sensor). The remainder of the light may pass through the beam splitter 1130 and travel through a filter 1158 to image sensor 1120 (white light image sensor). By locating the lens system 1156 between the tissue 1150 and the beam splitter 1130, the lens system may be along the shared portion of the optical path for the white light and laser speckle image sensors, such that only a single lens system may be required in the system.

Having a single lens system, rather than different lens systems for each of the two sensors (one lens system along the white light imaging path and one lens system along the laser speckle sensor path, each located between the beam splitter and the respective image sensor, as shown for example in FIG. 11A), may allow for a significant reduction in the size, complexity, and cost of the imaging system. It should be appreciated that in other variations, the locations of one or more optical elements such as the filters, lens systems, aperture, and beam splitter may be suitably rearranged.

Figure 12A:
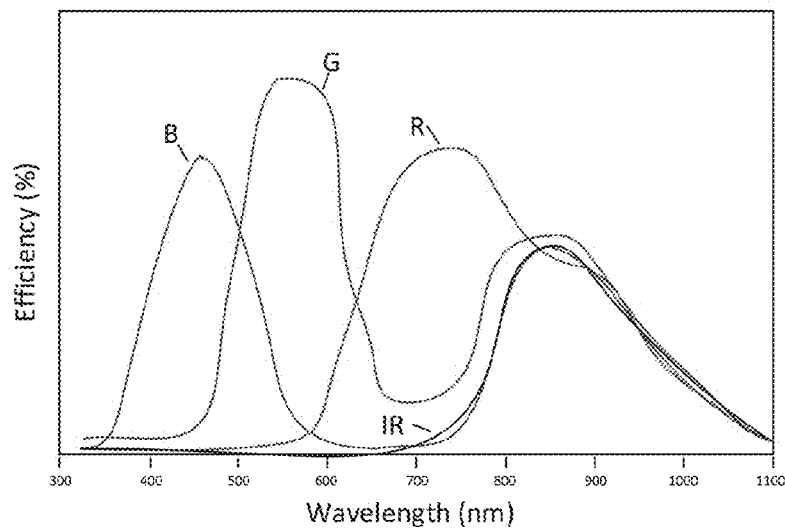
FIGS. 12A and 12B illustrate exemplary spectral responses of RGBIR and RGBW image sensors, respectively.
Figure 12B:
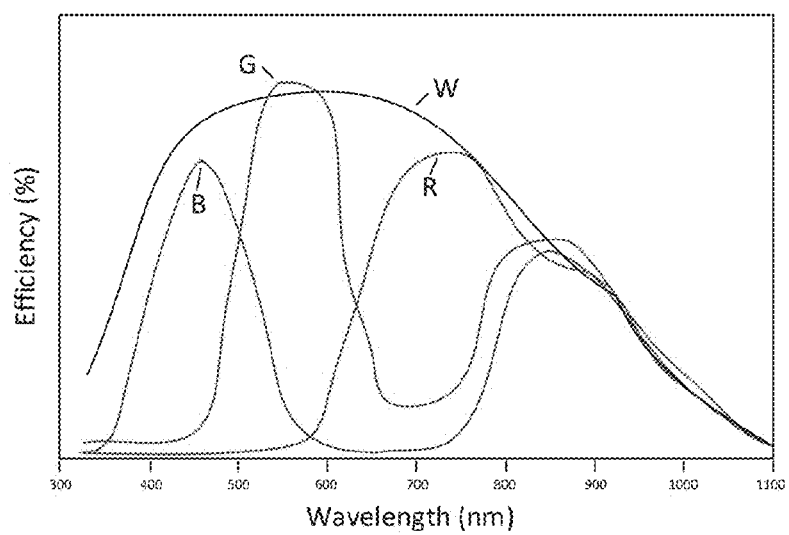

In some variations, the white light image sensor 1120 may comprise a Bayer filter. In these variations, the conversion of the raw white light image sensor data to the color image may be performed using a Bayer conversion algorithm. In other variations, the white light image sensor 1120 may be an RGBW sensor (also known as a W-RBG sensor), an RGBIR sensor (also known as an IR-RGB sensor), or a similar type of sensor. These sensors comprise a filter having a modified Bayer pattern that replaces a green pixel with a white (i.e., wide wavelength range) or infrared pixel. Exemplary spectral responses of the different pixels in an RGBIR sensor are shown in FIG. 12A, and exemplary spectral responses of the different pixels in an RGBW sensor are shown in FIG. 12B. It should be appreciated that in yet other variations, the white light image sensor may not be a color image sensor, and may instead comprise one or a plurality of monochrome image sensors.

The use of a sensor with a white or infrared pixel may be advantageous in additionally allowing calculation of the amount of ambient light without the need for a band-pass or long-pass filter. When using RGBW or RGBIR sensors, the signal from the white or infrared pixel may be compared to the signals from the other color pixels (RGB) to determine the amount of ambient light, which can be used to adjust the speckle image. Generally, this comparison may be done while the coherent illumination source is off. Because the speckle field may add a large contrast between the pixels, this comparison may usually be done within a larger scale kernel of pixels, instead of within a 2×2-pixel Bayer pattern pixel group. The amount of visible light may be determined by statistically comparing the color channels within such a kernel. In some variations, calibration data, such as an image from a white surface, may be used to optimize the statistics of the comparison. In one illustrative example, comparing the signal from the white or infrared pixel to the signals from the other color pixels may include averaging the values for each color channel in a 14×14 pixel kernel, calculating the amount of visible light using a weighted sum of each color channel, and comparing the amount of visible light to the average value of the W/IR channel inside the same pixel kernel.

In some variations in which the system uses two separate image sensors 1110 and 1120 for speckle and white light images, the white light image sensor may be an RGBW- or RGBIR-type sensor, and its field of view may be larger than the illumination area of the coherent light source 1141. The RGBW or RGBIR image sensor may be modified to reduce the amount of near-infrared light that reaches the RGB pixels. FIG. 13 illustrates an exemplary spectral response of such a modified RGBIR image sensor. Thus, such a modified sensor may have no or reduced sensitivity to near-infrared light for the RGB pixels, while the W or IR pixel is sensitive to near-infrared light as usual. Alternatively, in some variations, the system may use two separate image sensors 1110 and 1120 for speckle and white light images, respectively, but with typical, unmodified RGBW or RGBIR filters. In these variations, the speckle noise may be removed using image processing and/or by pulsing the coherent light source as discussed above. In some variations, the white light image sensor may receive light in the wavelength of the coherent light source returning from the illuminated region of tissue and directed by a beam splitter 1130, as shown in the arrangement of FIG. 11A, which is not wavelength dependent (e.g., a polarizing beam splitter). In other variations, the white light and speckle image sensors may have separate optical paths, as described above with reference to FIG. 11B. The RGB channels of the white light image sensor may be used to generate a white light image while the W or IR channels may be used to determine ambient light. As described previously, ambient light detected using the W/IR pixels may be used to adjust the speckle image to compensate for ambient light. Some variations may pulse the laser and/or have an imaging area outside the illumination area for further improvement of the ambient light detection.

Turning back to FIG. 1, the control unit 210 may comprise a microprocessor, a microcontroller, or any other state machine capable electronics which controls the sequence of events inside the imaging system. For example, the control unit 210 may configure the image sensor(s) and set parameters such as exposure time and gain. Some of these parameters may be adjusted continuously, e.g., before each frame or every second. The exposure time may be adjusted continuously in embodiments where the same sensor is used for the white light image and the speckle image. The gain may also be continuously adjusted during acquisition of the speckle image to adjust the brightness of the image and prevent saturation, because the exposure time normally is kept fixed. In some variations, the power of the coherent light source may be controlled to adjust the brightness of the speckle image.

The processing of the speckle image(s) may be performed using the processing unit 220. In some variations, the processing unit may comprise a GPU for performing calculations using a massively parallelized algorithm. In another variation, the processing may be done using a FPGA (field programmable gate array) or an ASIC. In yet another variation, the processing may be done using DSP or any other CPU or microprocessor. The processing may be split into several processing units each having different embodiments. It may also be possible to combine the control unit 210 and the processing unit 220 in the same unit.

The operator of the imaging system (e.g., a health care professional, such as a doctor, nurse, or technician) may use the system to visualize or measure blood flow and perfusion. The methods and systems described herein may be used in many clinical applications such as, for example, wound care (e.g., burn care, chronic ulcers, bed sores, skin grafting, or hyperbaric chamber), surgery (e.g., breast reconstruction, skin flaps, extremity perfusion, or aesthetic surgery), or cardiovascular applications (e.g., diabetes, rheumatology, or peripheral vascular disease).

In operation, the operator may first switch on the imaging system. After startup, the operator may choose to enter certain data such as, for example, patient information, or change settings using the user interface (human-machine-interface or "HMI"). When this step is completed or omitted, the system may begin visualization mode. In this mode, the camera may continuously take and process images. The image (e.g., a perfusion image) may be displayed on the system display. The operator may orient and position the system to visualize the area of interest. The operator may be able to see the perfusion of the area of interest in real time. In some variations, the operator may be able to take snapshots and/or videos of the perfusion, which may be stored for later use. For example, snapshots or videos may be stored on an internal or external non-volatile memory for later access or export. In some of these variations, the snapshots or videos may be stored together with meta-data (such as patient information and/or date/time) and/or a white light image of the area of interest.

While the present invention has been illustrated and described in connection with various embodiments shown and described in detail, it is not intended to be limited to the details shown, since various modifications and structural changes may be made without departing in any way from the scope of the present invention. For the purpose of clarity and a concise description features are described herein as part of the same or separate embodiments, however, it will be appreciated that the scope of the disclosure includes embodiments having combinations of all or some of the features described. Various modifications of form, arrangement of components, steps, details and order of operations of the embodiments illustrated, as well as other embodiments of the invention may be made without departing in any way from the scope of the present invention, and will be apparent to a person of skill in the art upon reference to this description. It is therefore contemplated that the appended claims will cover such modifications and embodiments as they fall within the true scope of the invention. For the terms "for example" and "such as," and grammatical equivalences thereof, the phrase "and without limitation" is understood to follow unless explicitly stated otherwise. As used herein, the singular forms "a," "an," and "the" include plural referents unless the context clearly dictates otherwise.

What is claimed is:

1. A method for imaging tissue of a subject, the method comprising:

illuminating the tissue with a coherent light having a coherent wavelength;
acquiring image data of the tissue using a color image sensor, said color image sensor having pixels, some of the pixels corresponding to a first color, some of the pixels corresponding to a second color, and some of the pixels corresponding to a third color; and
processing the image data using laser speckle contrast analysis while correcting for differences in sensitivity of color pixels at the coherent wavelength to generate a perfusion image of the tissue wherein the correction includes applying a first correction factor to the first color pixels, a second correction factor to the second color pixels and a third correction factor to the third color pixels.

2. The method of claim 1 wherein the correction factors are determined during image data acquisition.

3. The method of claim 1 further comprising alternating the coherent light between a turned on state and a turned off state during image data acquisition.

4. The method of claim 3 wherein the image data acquired during the turned off state of the coherent light comprises white light image data to generate a white light image.

5. The method of claim 1 further comprising displaying the perfusion image.

6. The method of claim 1 wherein the coherent wavelength ranges from about 750 nm to about 850 nm.

7. A method for imaging tissue of a subject, the method comprising:
illuminating the tissue with a coherent light having a coherent wavelength;
acquiring image data of the tissue using a color image sensor; and
processing the image data using laser speckle contrast analysis while correcting for differences in sensitivity of different color pixels at the coherent wavelength to generate a perfusion image of the tissue wherein correcting for difference in sensitivity of color pixels at the coherent wavelength comprises changing color channel dependent analog or digital gain of the image sensor.

8. A method for imaging tissue of a subject, the method comprising:
illuminating the tissue with a coherent light having a coherent wavelength;
acquiring image data of the tissue using a color image sensor; and
processing the image data using laser speckle contrast analysis while correcting for differences in sensitivity of color pixels at the coherent wavelength to generate a perfusion image of the tissue wherein correcting for differences in sensitivity of color pixels at the coherent wavelength comprises calculating separate speckle images based on each set of like color pixels, and combining the calculated speckle images to calculate the perfusion image.

9. A system for imaging tissue of a subject, the system comprising:
a coherent light source to generate coherent light having a coherent wavelength;
a color image sensor to acquire image data of the tissue, said color image sensor having pixels, some of the pixels corresponding to a first color, some of the pixels corresponding to a second color, and some of the pixels corresponding to a third color; and
a processor to process the image data using laser speckle contrast analysis while correcting for differences in sensitivity of color pixels at the coherent wavelength to generate a perfusion image of the tissue wherein the correction includes applying a first correction factor to the first color pixels, a second correction factor to the second color pixels and a third correction factor to the third color pixels.

10. The system of claim 9 wherein the correction factors are determined during manufacturing of the system, calibration of the system, use of the system, or a combination thereof.

11. The system of claim 9 further comprising a control unit in communication with the color image sensor, the processor, or a combination thereof to control the color image sensor, the processor, the coherent light source, or a combination thereof.

12. The system of claim 9 further comprising means to alternate the coherent light between a turned on state and a turned off state during image data acquisition.

13. The system of claim 12 wherein the image data acquired during the turned off state of the coherent light comprises white light image data to generate a white light image.

14. The system of claim 13 wherein the image data comprises ambient light image data, and the processor further generates an ambient light image.

15. The system of claim 13 further comprising a display to display the perfusion image and the white light image.

16. The system of claim 9 wherein the coherent wavelength ranges from about 750 nm to about 850 nm.

17. The system of claim 9 further comprising a display to display the perfusion image.

18. A system for imaging tissue of a subject, the system comprising:
a coherent light source to generate coherent light having a coherent wavelength;
a color image sensor to acquire image data of the tissue; and
a processor to process the image data using laser speckle contrast analysis while correcting for differences in sensitivity of color pixels at the coherent wavelength to generate a perfusion image of the tissue wherein correcting for difference in sensitivity of color pixels at the coherent wavelength comprises changing color channel dependent analog or digital gain of the image sensor.

19. A system for imaging tissue of a subject, the system comprising:
a coherent light source to generate coherent light having a coherent wavelength;
a color image sensor to acquire image data of the tissue; and
a processor to process the image data using laser speckle contrast analysis while correcting for differences in sensitivity of color pixels at the coherent wavelength to generate a perfusion image of the tissue wherein the correction for differences in sensitivity of color pixels at the coherent wavelength comprises a calculation of separate speckle images based on each set of like color pixels, and combining the calculated speckle images to calculate the perfusion image.

* * * * *